United States Patent [19]

Leuchtenberger et al.

[11] Patent Number: 4,530,903

[45] Date of Patent: Jul. 23, 1985

[54] L-2-HYDROXY-4-METHYLPENTANOIC ACID-DEHYDROGENASE, PROCESS FOR OBTAINING IT AND ITS USE

[75] Inventors: Wolfgang Leuchtenberger, Bruchköbel; Maria-Regina Kula, Wolfenbüttel; Werner Hummel, Braunschweig; Horst Schütte, Salzgitter, all of Fed. Rep. of Germany

[73] Assignee: Degussa Aktiengelleschaft, Frankfurt, Fed. Rep. of Germany

[21] Appl. No.: 531,725

[22] Filed: Sep. 13, 1983

[30] Foreign Application Priority Data

Sep. 14, 1982 [DE] Fed. Rep. of Germany ....... 3234022

[51] Int. Cl.$^3$ .......................... C12P 11/00; C12P 7/40; C12N 9/04; C12R 1/225
[52] U.S. Cl. .................................... 435/130; 435/136; 435/190; 435/853
[58] Field of Search ............... 435/130, 136, 146, 190, 435/853

[56] References Cited

U.S. PATENT DOCUMENTS 4,326,031 4/1982 Wandrey et al. ................... 435/146

*Primary Examiner*—Lionel M. Shapiro
*Attorney, Agent, or Firm*—Cushman, Darby & Cushman

[57] ABSTRACT

The purpose of the invention is the new enzyme L-2-hydroxy-4-methylpentanoic acid-dehydrogenase and its recovery from Lactobacillus confuses. The new enzyme can be used to enzymatically change L-2-hydroxy-4-methylpentanoic acid and various other L-2-hydroxy-carboxylic acids into the corresponding 2-ketocarboxylic acids or 2-keto-4-methylpentanoic acid and various other 2-ketocarboxylic acids into the corresponding L-2-hydroxycarboxylic acids.

7 Claims, No Drawings

L-2-HYDROXY-4-METHYLPENTANOIC ACID-DEHYDROGENASE, PROCESS FOR OBTAINING IT AND ITS USE

SUMMARY OF THE INVENTION

An object of the invention is a L-2-hydroxy-4-methylpentanoic acid-dehydrogenase which is characterized by the following properties:

(a) specific activity against L-2-hydroxy-4-methylpentanoic acid, (b) dependent from nicotinamide-adeninedinucleotide (NAD), (c) temperature-optimum of the activity 40° to 60° C., (d) temperature optimum of the stability $\leq 40°$ C., (e) pH-optimum for the dehydrogenation reaction 8.0 to 8.5, (f) pH-optimum for the reduction reaction around 7.0, (g) pH stability region 6.5 to 8.5, (h) Michaelis-constant ($K_m$ value) against L-2-hydroxy-4-methylpentanoic acid $0.62 \times 10^{-3}$M, and (i) additional activity against L-2-hydroxypentanoic acid, L-2-hydroxyhexanoic acid, and L-2-hydroxy-4-(methylmercapto)-butyric acid.

A further object of the invention is a process for the recovery of the new L-2-hydroxy-4-methylpentanoic acid-dehydrogenase which is characterized by growing Lactobacillus confusus (DSM 20196) in an aqueous nutrient medium which contains a source of carbon and nitrogen, as well as mineral salts, growth materials and vitamins and has at the beginning of the culturing a pH of 6.5, after the end of the culturing the cells harvesting by centrifugation, solubilizing the product in a suspension buffered to pH 7 and obtaining the enzyme from the extract.

Finally, an object of the invention is also the use of the new enzyme for the enzymatic conversion of L-2-hydroxy-4-methylpentanoic acid, L-2-hydroxypentanoic acid, L-2-hydroxyhexanoic acid, or L-2-hydroxy-4-(methylmercapto)-butyric acid into the corresponding 2-ketocarboxylic acid or from 2-keto-4-methylpentanoic acid, 2-ketopentanoic acid, 2-ketohexanoic acid, or 2-keto-(4-methylmercapto)-butyric acid into the corresponding L-2-hydroxy-carboxylic acid.

The new enzyme exhibits a specific activity against L-2-hydroxy-4-methylpentanoic acid and an additional activity against various other L-2-hydroxy-carboxylic acids, especially against L-2-hydroxy-pentanoic acid, L-2-hydroxyhexanoic acid, and L-2-hydroxy-4-(methylmercapto)-butyric acid. It is coenzyme dependent and for the dehydrogenation reaction requires the presence of nicotinamide-adenine-dinucleotide (NAD+) and for the reverse reaction, i.e., the hydrogenation of the 2-ketocarboxylic acid, the presence of the hydrogenated nicotinamide-adeninedinucleotide (NADH). The optimum temperature of the activity is in the range between 40° and 60° C., the optimum temperature of the stability is at a maximum of about 40° C., the optimum pH for the dehydrogenation reaction is at about 8.0 to 8.5, and for the reverse reaction is about 7.0. The new enzyme is most stable in the pH range between about 6.5 and 8.5. The Michaelis constant ($K_M$ value) for the substrate L-2-hydroxy-4-methylpentanoic acid is $0.62 \times 10^{-3}$M.

DETAILED DESCRIPTION

The new enzyme can be obtained from a microorganism obtainable from the German Collection of Microorganisms (DSM) in Gottigen, namely Lactobacillus confuses (Catalogue Number 20196 DSM). The culturing of the microorganism is carried out suitably in the nutrient medium in the Catalogue of the German Collection of Microorganisms or in the following specified nutrient media. Below there is described the method of obtaining the new enzyme from Lactobacillus confusus (DSM 20196).

1. Culturing of the Microorganism

For the culturing Lactobacillus confusus (DSM 20196) was grown on the following medium:

| | |
|---|---|
| Glucose | 20 g |
| Yeast extract | 10 g |
| Meat extract | 0.5 g |
| Sodium acetate | 5 g |
| $K_2HPO_4$ | 2 g |
| $MgSO_4$ | 0.2 g |
| $MnSO_4$ | 0.05 g |
| Deionized Water to | 1 liter |

The pH of this solution was adjusted to 6.5, then it was sterilized for 15 minutes at 121° C. (2 bar).

For the culturing 5 ml of medium in a test tube were inoculated with a loop full of Lactobacillus confusus from stab agar tubes and incubated for 16 to 20 hours at 30° C. 4 ml of the grown culture were then used as inoculant culture for 200 ml of medium (in 500 ml Erlenmeyer flasks).

After 20 to 24 hours, there were used 200 ml of this as a preliminary culture for a 10 liter fermenter in order that there could then be inoculated 200 liters and subsequently 5,000 liters. The pH which sank in the course of the growth was held at 5.0 in the fermenters with concentrated ammonia. Toward the end of the logarithmic growth phase the culture was cooled and the cells harvested by centrifugation. The biomass can be stored at $-20°$ C. intermediately for several weeks or months without loss of activity.

2. Recovery and Purification of the Enzyme (a) Crude Extract 24 kg of Lactobacillus confusus cells (wet mass) were suspended in 100 mM of phosphate buffer to obtain a pH 7.0. The buffer solution contained 0.1% (v/v) of 2-mercaptoethanol. The final volume of 60 liters corresponds to a cell suspension of about 40%. The cells were broken up in a continuously operating industrial glass bead ball mill (NETZSCH LME 20). The horizontally arranged grinding container having a capacity of 22.7 liters was filled with 0.55 to 0.85 mm glass beads so that there resulted an apparent volume of 19.3 liters (85%). The breaking up was carried out at 1200 rpm and a flow through rate of 100 l/h. The cooling jacket of the grinding container was cooled with ethylene glycol solution having a temperature of $-10°$ C. during the running, in order to substantially avoid a heating of the product. After two run throughs, there was reached a degree of disintegration of about 90%. The pH of the suspension fell during the homogenization to 6.3.

(b) Liquid-Liquid Distribution

With the first distribution step, the cell debris should be separated from the crude extract. For this purpose, an aqueous 2-phase system was produced which contained 18% (w/w) polyethylene glycol 1500, 7% (w/w)

phosphate buffer for a pH of 7.0 to 60 liters of crude extract in a 120 kg-system. In order to obtain a good distribution, the 2-phase system was stirred for 2 hours the D-lactate-dehydrogenase. The active fractions were concentrated by ultrafiltration and stored at 4° C. The purification steps are summarized in Table 1.

TABLE 1

| | Purification of L-2-Hydroxy-4-methylpentanoic acid-Dehydrogenase | | | | | |
|---|---|---|---|---|---|---|
| Purification Step | Volume l | Protein g | Total Activity U | Spec. Activity U.mg$^{-1}$ | Yield % | Enrichment-fold |
| Crude extract | 60 | 1518 | 264 000 | 0.17 | 100 | 1 |
| Upper Phase I | 86 | 955 | 259 700 | 0.27 | 98.4 | 1.6 |
| Upper Phase II | 71 | 70 | 172 500 | 2.46 | 65.3 | 14.5 |
| Lower Phase III | 82 | 48 | 159 800 | 3.33 | 60.5 | 19.6 |
| Diafiltration | 0.5 | 26 | 133 000 | 5.12 | 50.4 | 30.1 |
| DEAE-Cellulose | 0.95 | 3.6 | 107 000 | 30.1 | 40.5 | 177.1 | and subsequently separated with a plate separator (type Gyrotester B of α-Laval). The flow through rate during the separation of the phases was 60 l/h, there were employed 4 13.5 mm adjusting screws. The upper phase (86 liters) contained practically the entire activity (yield 98.4%) of L-2-hydroxy-4-methylpentanoic acid-dehydrogenase. The lower layer contained the cell debris and was discarded.

The enzyme containing upper phase of the preceding step was treated with 2% (w/v) polyethylene glycol 10,000, 10% (w/v) phosphate buffer for a pH of 6.0 and 0.2M sodium chloride, calculated on the final volume of 172 l, and was stirred for 2 hours. The polyethylene glycol-salt solution forming was deposited in a glass container, the separation was complete in about 1 hour. In this distribution step, a large number of proteins were extracted into the lower phase, among others the greatest portion of the D-lactate-dehydrogenase present in excess, while the L-2-hydroxy-4-methylpentanoic acid-dehydrogenase to a large extent remained in the upper phase (71 liters). The separation of the phases was carried out by allowing the lower phase to drain off.

The upper phase of the preceding step was treated with 10% (w/v) of phosphate for a pH of 6.0 and 0.2 moles of sodium chloride and then filled up to 142 liters. After a stirred time of 2 hours, the phases were allowed to separate in a settling tank. The L-2-hydroxy-4-methylpentanoic acid-dehydrogenase activity was located in the lower phase (82 liters).

(c) Diafiltration

The lower phase was concentrated in a Romicon hollow fiber cartridge (type HF 30-20-GM-80) and diafiltered through addition of phosphate buffer for a pH of 6.5 to a final concentration of 200 mmoles. Subsequently, the enzyme solution was concentrated with an Amicon-hollow fiber cartridge (Hl P30) to 500 ml.

(d) DEAE-Cellulose Chromatography

The concentrated and diafiltered enzyme was pumped to a 5×40 cm column which was packed with Whatman Cellulose DE 52. The DEAE cellulose was equilibrated against a buffer which contained 200 mmoles of phosphate buffer for a pH of 6.5 and 0.1% (v/v) of 2-mercaptoethanol. The column was first washed with 2.5 liters of starting buffer and the enzyme subsequently eluted with a linear gradient (2×2 liters) of 0 to 1 mole of sodium chloride in starting buffer. The L-2-hydroxy-4-methylpentanoic acid-dehydrogenase was eluted with 0.3 mole of sodium chloride and was completely separated from the residual constituents of The molecular weight of the L-2-hydroxy-4-methylpentanoic acid-dehydrogenase was determined by gel filtration on Sephacryl S 300 superfine to be about 125,000±15,000 Dalton. The specific activity of the enzyme was improved with the gel filtration to a value above 100 U.mg$^{-1}$.

In the following Example 1 the activity of an enriched L-2-hydroxy-4-methylpentanoic acid-dehydrogenase preparation was tested for the conversion of various 2-hydroxycarboxylic acids into the corresponding 2-ketocarboxylic acids. In each case, there was measured the maximal initial reaction velocity $V_{max}$ and the $K_M$ value.

The process can comprise, consist essentially of, or consist of the recited steps with the stated materials.

EXAMPLE 1

The reaction velocity for the dehydrogenation of L-2-hydroxy-4-methylpentanoic acid was investigated in the following test mixture: 0.099 molar phosphate buffer for pH 8.0, 3 mmoles of NAD$^+$ and limiting amounts of enzyme. The concentration of the L-2-hydroxy-4-methylpentanoic acid was varied in the range of 0.2 to 10 millimoles. The increase of the extinction through the NADH formed was measured at 340 nm. There was marked a zero point which was obtained when the test was run without L-2-hydroxy-4-methylpentanoic acid. The enzymatic activity was given in International units U (units) whereby a U means the formation of 1 μmol NADH/min and ml. In a corresponding manner, the enzymatic activity against other 2-hydroxycarboxylic acids was determined. The concentration of the corresponding 2-hydroxycarboxylic acids in the test was varied between 0.2 and a maximum of 100 millimoles. By increasing the substrate concentration, the maximum beginning reaction velocity $V_{max}$ was ascertained. The Michaelis constant ($K_M$ value) corresponds to the substrate concentration in moles/liter, at which the reaction velocity V amounts to half the maximum initial reaction velocity. The kinetic constants $V_{max}$ and $K_M$ were ascertained through non-linear regression of the Michaelis-Minten-Gleichung and are collected in Table 2.

The maximum initial reaction velocity $V_{max}$ with the dimension $\mu mol \times min^{-1} \times mg^{-1}$ results through the division of the volume activity (U/ml) which was measured at substrate saturation (as a rule $10 \times K_M$ unless otherwise specifically given) through the protein content of the enzyme solution employed.

TABLE 2

| Substrate | maximal beginning-reaction speed (μMol × min$^{-1}$ × mg$^{-1}$) | $V_{max} K_M$-Value* (M) |
|---|---|---|
| L-2-Hydroxy-4-methylpentanoic acid | 9.8 | 0.62 × 10$^{-3}$ |

TABLE 2-continued

| Substrate | maximal beginning-reaction speed ($\mu$Mol × min$^{-1}$ × mg$^{-1}$) | $V_{max}$ $K_M$-Value* (M) |
|---|---|---|
| DL-2-Hydroxy-4-methylpentanoic acid | 9.6 | $1.4 \times 10^{-3}$ |
| DL-2-Hydroxypentanoic acid | 7.9 (6 × $K_M$) | $3.55 \times 10^{-3}$ |
| DL-2-Hydroxyhexanoic acid | 11.8 (5 × $K_M$) | $4.5 \times 10^{-3}$ |
| DL-2-Hydroxy-4-(methylmercapto)-butyric acid | 1.2 | $11.0 \times 10^{-3}$ |

*With the enantiomer mixture the calculation was based on the total concentration.

The table shows that a series of 2-hydroxycarboxylic acids were oxidized to the 2-ketocarboxylic acid. In comparison of the constants found for the pure L-enantiomer and the D,L-mixture, it was clear that the D-component in the region of the measured concentration has no influence on the kinetic constants. At 100 millimoles substrate concentration on the contrary there was already noticed a clear substrate excess inhibition (Table 3).

The relative activities (U/ml) set forth in Table 3 were measured at substrate-final concentrations of 1 millimole, 10 millimoles, and 100 millimoles. In all cases, there was employed the same enzyme solution.

TABLE 3

| Substrate | Test Concentration | | |
|---|---|---|---|
| | 1 mM (U/ml) | 10 mM (U/ml) | 100 mM (U/ml) |
| L-2-Hydroxy-4-methylpentanoic acid | 28.4 | 49.7 | 5.0 |
| DL-2-Hydroxy-4-methylpentanoic acid | 16.6 | 39.8 | 2.9 |
| DL-2-Hydroxypentanoic acid | 6.2 | 31.2 | 5.3 |
| DL-2-Hydroxyhexanoic acid | 8.4 | 39.5 | 3.9 |
| DL-2-Hydroxy-4-(methylmercapto) butyric acid | 0.46 | 2.7 | 5.1 |

The dependency of the reaction velocity on the NAD+ concentration was ascertained in a test mixture which contained 0.1 molar phosphate buffer for pH 8.0, 6.3 millimoles of L-2-hydroxy-4-methylpentanoic acid and limiting amounts of enzyme. The NAD+ concentration was varied in the range of 0.05 to 7.0 millimoles.

The $K_M$ value for NAD+ was ascertained by non-linear regression of the Michaelis-Menten equation and was $3.3 \times 10^{-4}$ moles.

In the following Example 2, the activity of an enriched L-2-hydroxy-4-methylpentanoic acid-dehydrogenase preparation was examined for the conversion of various 2-ketocarboxylic acids into the corresponding 2-hydroxycarboxylic acids. In each case, there was again measured the maximal beginning reaction velocity $V_{max}$ and the $K_M$ value.

EXAMPLE 2

The reaction velocity for the reaction of 2-keto-4-methylpentanoic acid to L-2-hydroxy-4-methylpentanoic acid was ascertained in the following test mixture: 0.1 M phosphate buffer for pH 7.0, 0.235 millimoles NADH and limiting amounts of enzyme. The concentration of the 2-keto-4-methylpentanoic acid was varied in the range of 0.01 to 10 millimoles. The reaction was followed with a photometric test in which the decrease of the extinction of NADH was measured at 340 nm. There was marked a zero point which was obtained by running the test without 2-keto-4-methylpentanoic acid. The enzyme activity was stated in international units whereby a U indicates the consumption of 1 $\mu$M NADH/min and ml. In a corresponding manner there was determined the enzyme activity against other 2-ketocarboxylic acids. The keto acid concentration in each case was varied in the range of 0.01 to a maximum of 10 millimoles. The maximal initial reaction velocity was ascertained through the increase of the substrate concentration. The Michaelis constant ($K_M$ value) corresponds to the substrate concentration in moles/liter at which the reaction velocity V is half the maximum initial reaction velocity. The kinetic constants $V_{max}$ and $K_M$ were ascertained through nonlinear regression of the Michaelis-Menter equation and are summarized in following Table 4.

TABLE 4

| Substrate | Maximal Beginning Reaction Speed ($\mu$Mol × min$^{-1}$ × mg$^{-1}$) | $V_{max}$ $K_M$-value (M) |
|---|---|---|
| 2-Keto-4-methylpentanoic acid | 64 | $0.07 \times 10^{-3}$ |
| 2-Ketopentanoic acid | 87 (6 × $K_M$) | $0.25 \times 10^{-3}$ |
| 2-Ketohexanoic acid | 69 (6 × $K_M$) | $0.12 \times 10^{-3}$ |
| 2-Keto-4-(methylmercapto)-butyric acid | 28 | $0.21 \times 10^{-3}$ |

The table shows that a series of 2-ketocarboxylic acids can be reduced by the L-2-hydroxy-4-methylpentanoic acid-dehydrogenase to the corresponding L-2-hydroxycarboxylic acids.

The relative activities (U/ml) stated in Table 5 were measured at substrate final concentrations of 0.1 millimoles, 1 millimole, and 10 millimoles. In all cases, there was employed the same enzyme solution. At 10 millimoles in all substrates there was already noticeable a substrate excess inhibition.

The dependency of the reaction velocity on the NADH concentration was ascertained in a test mixture which contained 0.1 molar phosphate buffer for pH 7.0, 0.79 millimole of 2-keto-4-methylpentanoic acid, and limiting amount of enzyme. The NADH concentration was varied in the range of 0.01 to 0.33 millimoles. The $K_M$ value for NADH was ascertained through non-linear regression of the Michaelis-Menten equation and was $3.3 \times 10^{-5}$ moles.

TABLE 5

| Substrate | Test Concentration | | |
|---|---|---|---|
| | 0.1 mM (U/ml) | 1 mM (U/ml) | 10 mM (U/ml) |
| 2-Keto-4-methylpentanoic acid | 133 | 259 | 144 |
| 2-Ketopentanoic acid | 149 | 344 | 161 |
| 2-Ketohexanoic acid | 123 | 301 | 103 |
| 2-Keto-4-(methylmercapto)-butyric acid | 33 | 93 | 53 |

In following Example 3, finally there is described an experiment for the continuous enzymatic conversion of 2-keto-4-methylpentanoic acid into L-2-hydroxy-4- methylpentanoic acid according to the known process of Wandrey U.S. Pat. No. 4,326,031, the entire disclosure of which is hereby incorporated by reference and relied upon.

EXAMPLE 3

A flat membrane reactor held at a temperature of 25° C. and having a volume of 11.3 ml and which was equipped with a magnetic stirrer and an ultrafiltration membrane having a diameter of 62 mm having a nominal exclusion limit of 5,000 (supplier: Amicon, Witten; Type YM 5) for sterilization was rinsed for about 5 hours with aqueous formaldehyde solution and by means of a metering pump adjusted to a conveying speed of 11.3 ml/hour. Subsequently, during about a further 10 hours, the formaldehyde solution was removed by distillation of water. Then, there were likewise supplied at a conveying velocity of 11.3 ml/hour for about 10 hours over a sterile filter (0.2 $\mu$m) filtered substrate solution which contained 100 mmole/l of the sodium salt of 2-keto-4-methylpentanoic acid and 400 millimoles/l of sodium formate as well as 50 mmoles/l of potassium phosphate as buffer and was adjusted to pH 7 with sodium hydroxide solution. Thereupon, there was injected a further substrate dosing with a syringe before the sterile filter 4 ml of a solution of formate-dehydrogenase (activity 26.3 $\mu$mol/ml$\times$minute with formate as substrate, 25° C. and pH 8) in the form of an aqueous solution. Correspondingly, there were then injected in the form of an aqueous solution 0.5 ml of L-2-hydroxy-4-methylpentanoic acid dehydrogenase (activity 241.7 $\mu$mol/ml$\times$minute with 2-keto-4-methylpentanoic acid as substrate, 25° C. and pH 7). At the start of the reaction, there were further injected 2 ml of a coenzyme solution which contained 5.73 mmoles/l NADH tied to a polyethylene glycol having an average molecular weight of 20,000. After all catalysts were injected, the substrate stream was increased to 17 ml/hour so that there was an average residence time of 40 minutes. The reaction was followed continuously with the help of a polarimeter flow through cuvette installed in the filtrate stream. The pressure difference over the membrane at the beginning was 0.2 bar and increased in the course of 8 days of operation to 1.3 bar. Within an operating time of 191 hours (about 8 days), there were obtained 276 millimoles corresponding to 37 grams of L-2-hydroxy-4-methylpentanoic acid. The reaction fell from 93.9% to 76.3% (average reaction 85.1%). For the coenzyme, there resulted a deactivation of 9.29% per day, for the formate-dehydrogenase of 4.54% per day, for the L-2-hydroxy-4-methylpentanoic acid-dehydrogenase 4.68% per day. The space-time-yield over the entire duration of the operation was on the average 3.07 mol/l$\times$d or 411 g/l$\times$d. Per mole coenzyme (consumed), there were formed 71,800 moles of product. This correspond to a requirement of 68.9 mg NAD+ (native)/kg product. The enzyme requirement was 409 U formate-dehydrogenase/kg product or 617 U L-2-hydroxy-4-methylpentanoic acid-dehydrogenase/kg product. The average measured formate-dehydrogenase-activity during the entire operating time was 3.74 U/ml, in reference to the 2-hydroxy-4-methylpentanoic acid-dehydrogenase, 5.48 U/ml. The average coenzyme concentration was 0.48 mmole/l. The average reaction velocity over the entire operating time was 2.13 $\mu$mol/ml$\times$minute.

The entire disclosure of German priority application No. P 3234022.2 is hereby incorporated by reference.

What is claimed is:

1. The enzyme L-2-hydroxy-4-methylpentanoic acid-dehydrogenase having the following properties:
   (a) specific activity against L-2-hydroxy-4-methylpentanoic acid,
   (b) dependent from nicotinamide-adenine-dinucleotide (NAD),
   (c) temperature-optimum of the activity 40° to 60° C.,
   (d) temperature-optimum of the stability $\leq$40° C.,
   (e) pH-optimum for the dehydrogenation reaction 8.0 to 8.5,
   (f) pH-optimum for the reduction reaction around 7.0,
   (g) pH stability region 6.5 to 8.5,
   (h) Michaelis constant ($K_M$ value) against L-2-hydroxy-4-methylpentanoic acid $0.62 \times 10^{-3}$M, and
   (i) additional activity against L-2-hydroxypentanoic acid, L-2-hydroxyhexanoic acid, and L-2-hydroxy-4-(methylmercapto)-butyric acid.

2. A process for obtaining the L-2-hydroxy-4-methylpentanoic acid dehydrogenase enzyme of claim 1 comprising culturing *Lactobacillus confusus* (DSM 20196) in an aqueous nutrient medium containing a source of carbon, nitrogen, minerals, growth materials, and vitamis, employing a pH of about 6.5 at the beginning of the culturing and harvesting the cells after the culturing.

3. A process according to claim 2 wherein the cells are harvested by centrifuging, forming a suspension of the harvested material containing the dissolved enzyme at a pH vuffered to 7 and recovering the enzyme from the suspension.

4. A process of enzymatically converting L-2-hydroxy-4-methylpentanoic acid, L-2-hydroxypentanoic acid, L-2-hydroxyhexanoic acid, or L-2-hydroxy-4-(methylmercapto)- butyric acid into the corresponding ketocarboxylic acid comprising treating the hydroxy carboxylic acid with the enzyme of claim 1 together with a coenzyme for such reaction.

5. A process according to claim 4 wherein the coenzyme is NAD+.

6. A process of enzymatically converting 2-keto-4-methylpentanoic acid, 2-ketopentanoic acid, 2-ketohexanoic acid, or 2-keto-4-(methylmercapto)-butyric acid to the corresponding L-2 hydroxy carboxylic acid comprising treating the ketocarboxylic acid with the enzyme of claim 1 together with a coenzyme for such reaction.

7. The process according to claim 6 wherein the coenzyme is NADH.

* * * * *